United States Patent
Nasser-Ghodsi et al.

(10) Patent No.: US 6,677,586 B1
(45) Date of Patent: Jan. 13, 2004

(54) METHODS AND APPARATUS FOR ELECTRON BEAM INSPECTION OF SAMPLES

(75) Inventors: Mehran Nasser-Ghodsi, Hamilton, MA (US); Michael Cull, Wilmington, MA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/272,468

(22) Filed: Oct. 8, 2002

Related U.S. Application Data
(60) Provisional application No. 60/406,939, filed on Aug. 27, 2002, and provisional application No. 60/406,999, filed on Aug. 27, 2002.

(51) Int. Cl.⁷ .............. G01N 23/225; C23C 15/00; B68B 3/12; H01L 21/66
(52) U.S. Cl. .............. 250/310; 250/306; 250/307; 250/311; 250/492.1; 250/492.2; 250/492.3
(58) Field of Search ................ 250/310, 306, 250/307, 311, 492.1, 492.2, 492.3

(56) References Cited

U.S. PATENT DOCUMENTS

| | | | | |
|---|---|---|---|---|
| 3,867,192 A | * | 2/1975 | Hermans et al. | 430/296 |
| 3,984,583 A | * | 10/1976 | Hermans et al. | 430/296 |
| 4,496,449 A | * | 1/1985 | Rocca et al. | 204/298.36 |
| 4,645,977 A | * | 2/1987 | Kurokawa et al. | 315/111.21 |
| 5,532,494 A | * | 7/1996 | Kawanami et al. | 250/491.1 |
| 5,821,175 A | * | 10/1998 | Engelsberg | 438/795 |
| 6,319,321 B1 | * | 11/2001 | Hiraga et al. | 118/666 |
| 6,407,385 B1 | * | 6/2002 | Okada | 250/306 |
| 6,427,703 B1 | * | 8/2002 | Somekh | 134/1.1 |
| 6,444,381 B1 | * | 9/2002 | Singh et al. | 430/30 |
| 6,545,275 B1 | * | 4/2003 | Pearl et al. | 250/310 |
| 2002/0123161 A1 | * | 9/2002 | Ushiki et al. | 438/14 |
| 2002/0148961 A1 | * | 10/2002 | Nakasuji et al. | 250/311 |
| 2003/0102797 A1 | * | 6/2003 | Kajiwara | 313/486 |

* cited by examiner

Primary Examiner—John R. Lee
Assistant Examiner—Bernard Souw
(74) Attorney, Agent, or Firm—Beyer Weaver & Thomas LLP

(57) ABSTRACT

Methods and apparatus are providing for inspecting a test sample. An electron beam is tuned to cause secondary electron emissions upon scanning a target area. Reactive substances are introduced to etch and remove materials and impurities from the scan target. Residual components are evacuated. In one example, a laser is used to irradiate and area to assist in the removal of residual components with poor vapor pressure.

23 Claims, 9 Drawing Sheets

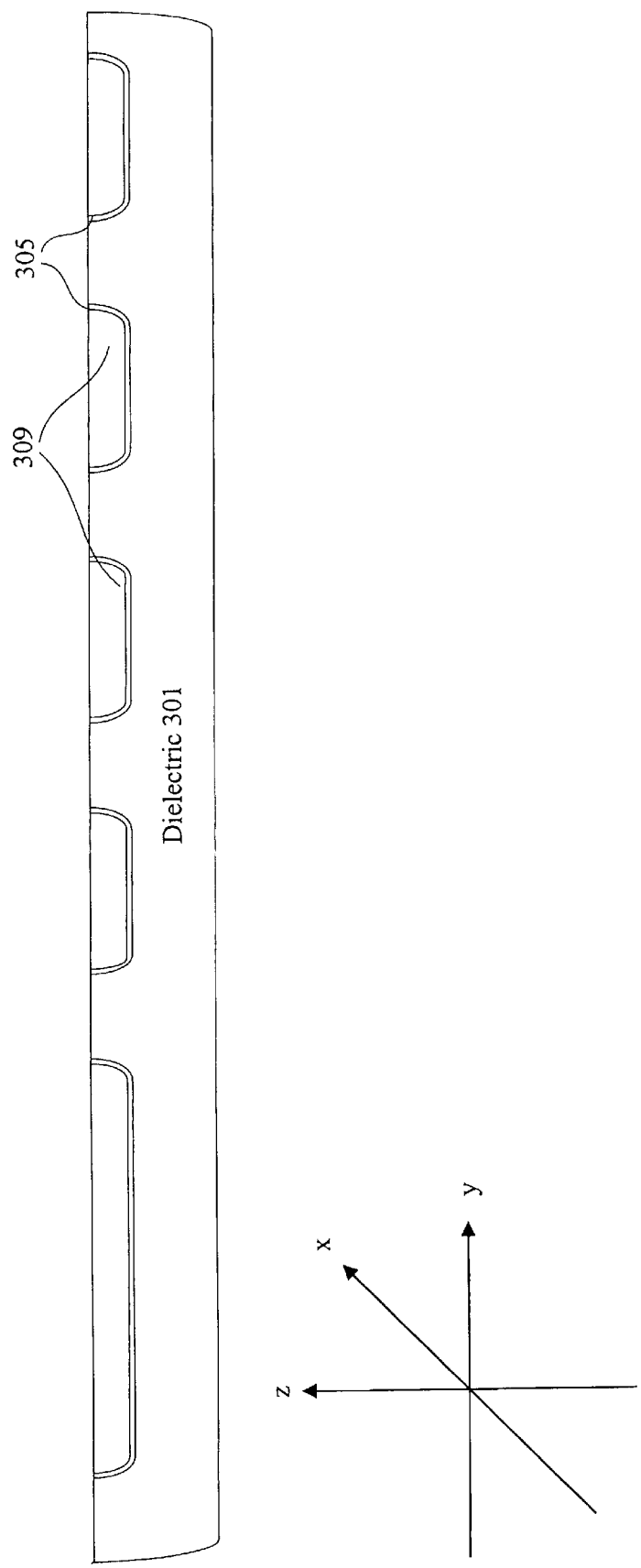

METHODS AND APPARATUS FOR ELECTRON BEAM INSPECTION OF SAMPLES

CROSS-REFERENCE TO RELATED APPLICATIONS

This application claims priority under U.S.C. 119(e) from U.S. Provisional Application No. 60/406,939, and U.S. Provisional Application No. 60/406,999, both filed on Aug. 27, 2002 and entitled, "METHODS AND APPARATUS FOR ELECTRON BEAM INSPECTION OF SAMPLES" by Mehran Nasser-Ghodsi and Michael Cull, the entireties of which are incorporated by reference in their entireties for all purposes. The present application is also related to concurrently filed U.S. patent application Ser. No. 10/272,467, entitled "METHODS AND APPARATUS FOR ELECTRON BEAM INSPECTION OF SAMPLES" by Mehran Nasser-Ghodsi and Michael Cull, the entirety of which are incorporated by reference in its entirety for all purposes.

BACKGROUND OF THE INVENTION

1. Field of the Invention

The present invention generally relates to the field of inspection and analysis of specimens. More particularly, the present application relates to gas assisted electron beam induced etching and cross sectioning.

2. Description of Related Art

Some techniques for cross sectioning and inspecting a test sample involve destructively cleaving a test sample in order to examine various elements in the sample. Other techniques for cross sectioning a test sample involve using focused ion beams, gas assisted ion beam induced etching, and high energy electron beam induced etching. However, ion beam based etching and deposition, using gallium, causes gallium poisoning, knock-on implant contamination, and sputtering of surface material onto the substrate and adjacent surfaces in the vacuum work chamber. In many cases, inspecting the sample prevents the sample from being used in production. In other cases, scanning the sample introduces contaminants such as gallium and carbon onto the test sample that interfere with the inspection of the sample.

Consequently, it is desirable to provide improved techniques and systems for characterizing and cross sectioning test samples.

SUMMARY

Methods and apparatus are providing for inspecting and cross sectioning a test sample. An electron beam is tuned to cause secondary electron emissions upon scanning a target area. Low reactivity substances, which are converted to elemental components with a high degree of reactivity, are introduced to etch and remove materials and impurities from the scan target. Residual components are evacuated. In one example, a laser is used to illuminate and thermally activate the area scanned by the electron beam, and to assist in the removal of residual components with poor vapor pressure.

In one embodiment, a method for inspecting a test sample is provided. A first scan target in a test sample is scanned by using an electron beam generator configured to emit particles with a first landing energy. The first landing energy causes secondary electron emissions from the first scan target. A reactive substance is introduced and a residual component is removed at the first scan target during a first period of time. The intensity of secondary electron emissions is measured during a second period of time.

In another embodiment, an apparatus for characterizing a sample is provided. The apparatus includes an electron beam generator operable to scan a first scan target in a sample using electrons with a first landing energy. The electron beam generator induces secondary electron emissions from the first scan target. A reactive substance injector is operable to introduce a reactive substance near the first scan target in order to remove carbon from the first scan target during periodic intervals. A secondary electron emission detector is configured to measure the intensity of secondary electron emissions between the periodic intervals.

These and other features and advantages of the present invention will be presented in more detail in the following specification of the invention and the accompanying figures that illustrate by way of example various principles of the invention.

BRIEF DESCRIPTION OF THE DRAWINGS

The invention may best be understood by reference to the following description taken in conjunction with the accompanying drawings. It should be noted that the drawings are illustrative of specific embodiments of the present invention.

FIG. 3 is a cross-sectional representation showing a plurality of layers.

DESCRIPTION OF SPECIFIC EMBODIMENTS

The techniques of the present invention provide nondestructive mechanisms for cross sectioning a test sample for inspection. In one embodiment, the test sample is a wafer having a plurality of integrated circuits. In order to inspect and measure characteristics of the test sample, an a highly focused electron beam is used to scan a target area. Various techniques are applied in conjunction with electron beam scans to etch away material, remove deposits at a scan target, and determine when enough material has been etched or removed.

According to various embodiments, materials exposed to electron beams tuned to specific landing energies emit particular intensities of secondary electrons. secondary electron emission detectors measure the intensity of secondary electrons emitted at a scan target to determine when material has been sufficiently etched or removed. This step is determined through monitoring the secondary electron energies, depending on the composition and yield of each layer. A significant transition in secondary electron energy relates directly to a transitional phase in the composition of a multi-layer substrate.

Several embodiments of the present invention are described herein in the context of exemplary multilevel integrated circuit structures, including semiconductor structures and overlying metallization or other interconnects, using various levels of conductors that are separated from each other and the substrate by dielectric layers. However, structures formed using other methods of semiconductor fabrication also fall within the scope of the present invention. The techniques of the present invention apply to all surfaces with and without specific layers.

Figure 1:
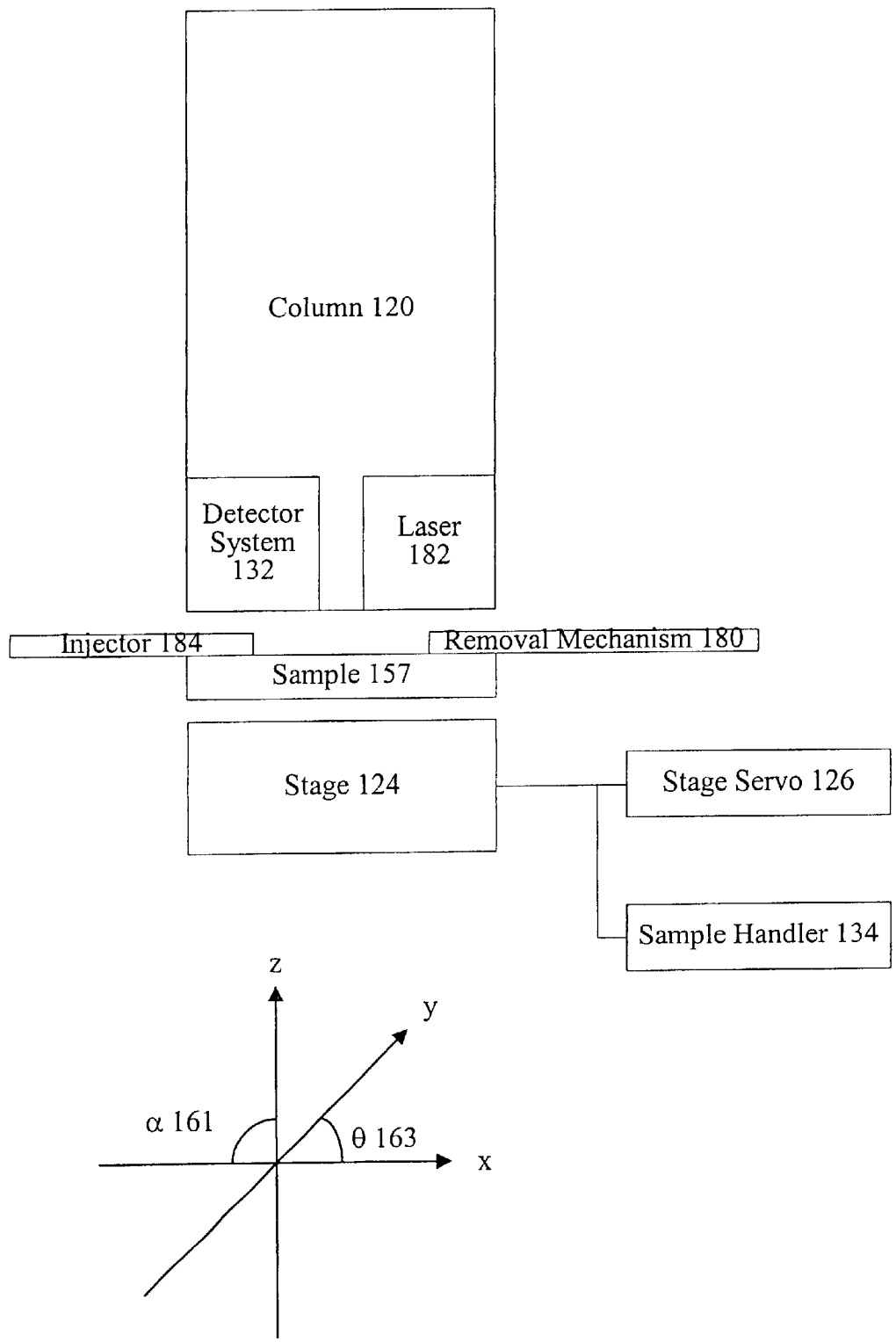
FIG. 1 is a diagrammatic representation of a system that can use the techniques of the present invention.

FIG. 1 is a diagrammatic representation of one example of a system that uses the techniques of the present invention. The detail in FIG. 1 is provided for illustrative purposes. One skilled in the art would understand that variations to the system shown in FIG. 1 fall within the scope of the present invention. For example, FIG. 1 shows the operation of an electron beam with a continuously moving stage. However, the test structures and many of the methods described herein are also useful in the context of other testing devices, including electron beams operated in step and repeat mode. As an alternative to moving the stage with respect to the electron beam, the electron beam may be moved by deflecting the field of view with an electromagnetic lens. Alternatively, the electron beam column and its secondary electron detectors can be moved with respect to the stage.

According to various embodiments, sample 157 is secured automatically beneath an electron beam 120. The sample handler 134 is configured to automatically orient the sample on stage 124. In one embodiment, the stage 124 is configured to have six degrees of freedom including movement and rotation along the x-axis, y-axis, and z-axis. In one embodiment, the stage 124 is aligned relative to the electron beam 120 so that the x-directional motion of the stage corresponds to the axis determined by the size of a target. For example, the sample 157 can be aligned so that the x-directional movement of the stage corresponds to the length of a target as viewed from the top of the sample. Furthermore, the sample can be tilted relative to the electron beam 120 along the axis determined by the length of the target. Similarly, the sample 157 can also be aligned so that the x-directional movement of stage corresponds to the size of a target. The sample can be tilted relative to the electron beam along the axis determined by the size of the target.

In one example, the stage lies on the x-y plane and the stage is tilted by varying the angle α 161. It should be noted that tilting the sample relative to the electron beam 120 can involve tilting the stage, tilting the column, deflecting the beam with a deflector to generate angles of incidence greater than the maximum incident angle at the limits of scanning, etc. It should also be noted that tilting the stage may involve varying the angle α 161 as well as rotating the stage along angle θ 163. Tilting the sample is one way of allowing scanning from different directions. Where the electron beam 120 is an electron beam, the sample can be aligned so that electrons can impinge a scan target from a wide variety of different angles.

Fine alignment of the sample can be achieved automatically or with the assistance of a system operator. The position and movement of stage 124 during the analysis of sample 157 can be controlled by stage servo 126. While the stage 124 is moving in the x-direction, the electron beam 120 can be repeatedly deflected back and forth in the y-direction. According to various embodiments, the electron beam 120 is moving back and forth at approximately 100 kHz.

According to various embodiments, a secondary electron emission detector 132 is aligned alongside the electron beam 120, a residual component removal mechanism 180, and a reactive substance injection mechanism 184. In one embodiment, the reactive substance injection mechanism 184 is arranged within 100 microns of the test sample to introduce a reactive gas onto the target. The reactive gas interacts with particles in the electron beam to etch away material at the scan target. The interaction leaves one or more residual components. According to various embodiments, the residual components are removed by using a residual component removal mechanism 180.

In one embodiment, the residual component removal mechanism 180 is a vacuum pump configured to remove the residual matter generated at the surface of the substrate which have adequate vacuum pressure at ambient temperatures. A tuned or broad band laser 182 can be used in conjunction with the residual component removal mechanism to allow evacuation of components with insufficient vapor pressure. The electron beam 120 and detector 132 as well as other elements such as the laser 182, the residual component removal mechanism 180, and the reactive component injector 184 can be controlled using a variety of processors, storage elements, and input and output devices.

Figure 2:
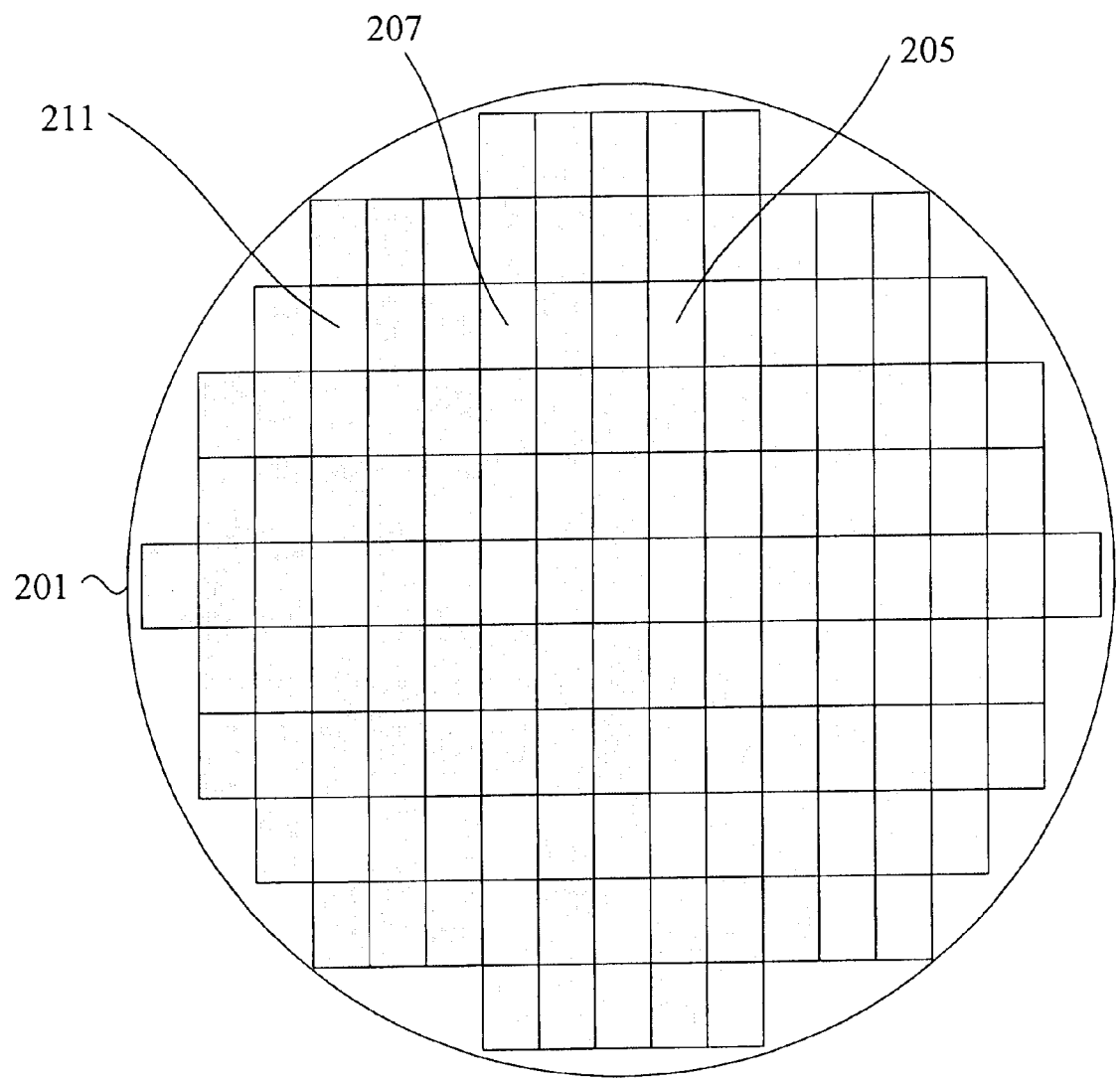
FIG. 2 is a diagrammatic representation of a wafer that may be the sample under test.

FIG. 2 is a diagrammatic representation of a wafer that may be a sample under test. A wafer 201 comprises a plurality of dies 205, 207, and 211. According to various embodiments, the techniques of the present invention for cross sectioning a test sample are performed after a metallization or thin film layer is deposited onto a wafer. The side of the wafer where the metallization process is performed is herein referred to as the top surface of the wafer. The wafer can be scanned to determine characteristics of various underlying layers. The ability to inspect and determine characteristics during the manufacturing process allows immediate modification of the manufacturing process.

The test methodologies of the present invention can be used as part of an advanced process control system, in which data from the testing process is provided to automated control systems for improving process yield. As an example, the techniques for measuring thicknesses can provide data to automated control systems that dynamically improve the metallization processes.

FIG. 3 is a diagrammatic representation of a cross-section of a test sample. The techniques of the present invention can be used to inspect a variety of aspects of a test sample. In one example, a resist layer can be etched in order to examine the materials beneath the resist layer. In another example, a substrate is etched to inspect a structures underneath the substrate. In still another example, the metallization or thin film layer 309 on top of a barrier layer 305 is etched to inspect the underlying barrier layer. According to various embodiments, the thin film layer 309 comprises a material such as copper (Cu) or aluminum (Al) and the barrier layer comprises a material such as tantalum (Ta) or tantalum nitride (TaN). For materials where the etch process is crystal angle dependent, this invesion allows for etching at an angle normal to the substrate in conjunction with a toggled (continuous rocking) beam.

The techniques of the present invention can also be used to remove deposits that may adversely impact chip performance. In one example, electron beam scans generate a carbon layer on top of a test sample. Hydrocarbon layers typically alter the intensity of secondary electron emissions detected. Furthermore, carbon layers can sometimes become an intermediate layer and prevent proper adhesion of a copper layer to a copper seed layer. According to various embodiments, electron beam assisted etching is used to remove carbon deposits during or in between scans. In some examples, the electron beam landing energy is set to induce secondary electron emissions from the scan target and to maximize the dissociative influence of the electron beam on the reactive or near reactive gas.

Figure 4A:
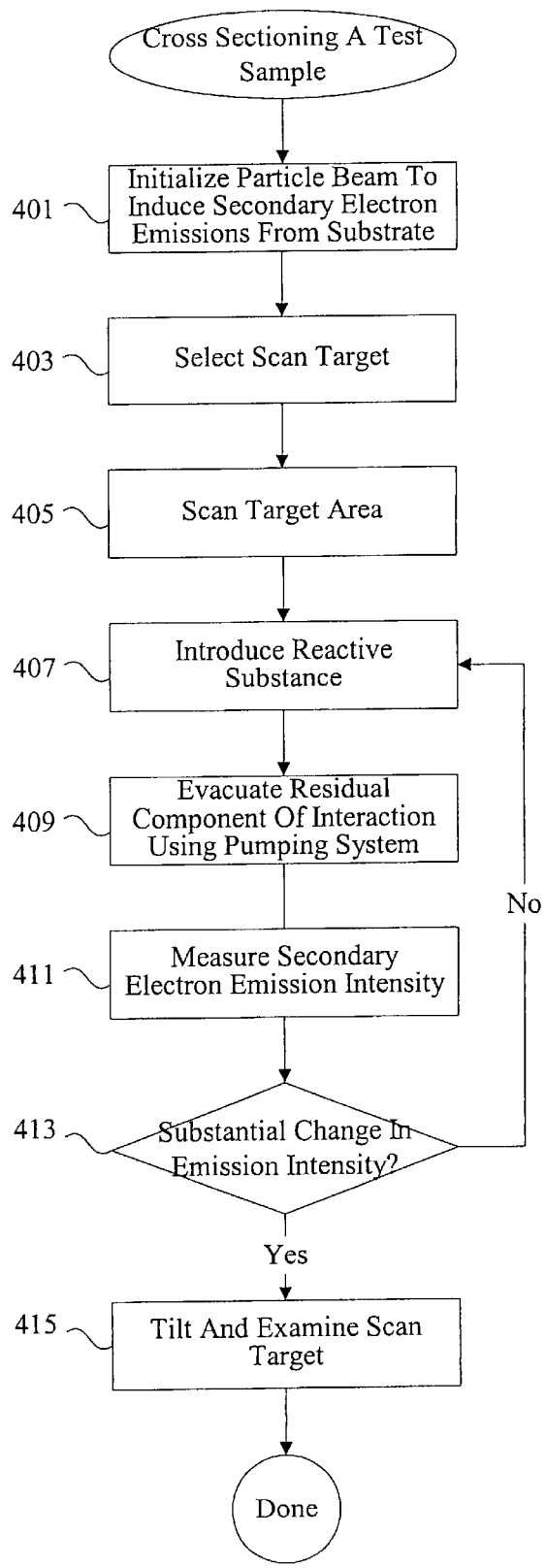
FIGS. 4A–4B are process flow diagrams showing the scanning of a sample.

FIG. 4A is a process flow diagram showing one example of a technique for cross sectioning a wafer. At 401, an electron beam is initialized to induce secondary electron emissions from a substrate. In one example, high beam currents and ultra low landing energies between 50 volts and 1000 volts are used to optimize secondary electron emissions. It should be noted, however, that other beam currents and other landing energies can be used based on the particular characteristics of a substrate. At 403, a particular scan target is selected and scanned at 405 using the electron beam. At 407, a reactive substance is introduced. According to various embodiments, the reactive substance is a non-reactive to a near reactive gas that interacts with the electrons from the electron beam, breaking into highly reactive components, which then interact with the substrate. In one embodiment, the reactive gas is $CCl_4$ or $CF_4$. $CCl_4$ or $CF_4$ breaks up into carbon and chlorine or fluorine components respectively to interact with the substrate to produce a chemical that has an appropriate pressure for evacuation by pumping system.

It should be noted that the reactive substance typically needs to be removed from the scan target because reactive substances interfere with the measurement of secondary electron emissions. If a reactive substance introduced is not subsequently removed, measurements of secondary electron emissions may be skewed. According to various embodiments, a reactive gas is injected using a reactive substance injection mechanism to within 100 microns of the substrate. In one embodiment, the dwell time of the reactive substance is controlled to allow an optimal period of time for the reactive substance to interact with the electrons and the substrate. In one example, the dwell time varies between hundreds of microseconds to hundreds of milliseconds. At 409, a residual component is evacuated using a pumping system.

It should be noted that the present application's reference to a particular singular entity includes plural entities, unless the context clearly dictates otherwise. Here, for example, multiple residual components may remain for evacuation by a pumping system. Any remnant of an interaction between a reactive substance, an electron beam, and a scan target is referred to herein as a residual component. In one example, a residual component is a gas that interferes with secondary electron emission measurements. At 411, secondary electron emission intensities are measured. Measuring intensity can include evaluating contrast and brightness components. One of the factors causing variations in secondary electron emission intensities is the material at the scan target. For example, the electron beam scanning the substrate would induce a different intensity of secondary electron emissions than an electron beam scanning the copper layer.

As material is etched from a scan target, secondary electron emissions and the current through the substrate are evaluated for information on what material is currently being scanned. At 413, if there is a substantial change in secondary electron emission intensity, or the current through the substrate, it is likely that the material has been etched away to reveal a different underlying material. If there is a substantial change in secondary electron emission intensity, or the current through the substrate, the scan target can then be examined from various angles at 415. If there is no change in secondary electron emission intensity, the reactive substance is again introduced at 407 to allow etching of more material.

It should be noted that although the above example has been described in the context of etching relating to a substrate, a variety of materials and layers can be removed using the techniques of the present invention. In one example, the resist layer is removed using a different reactive substance.

Figure 4B:
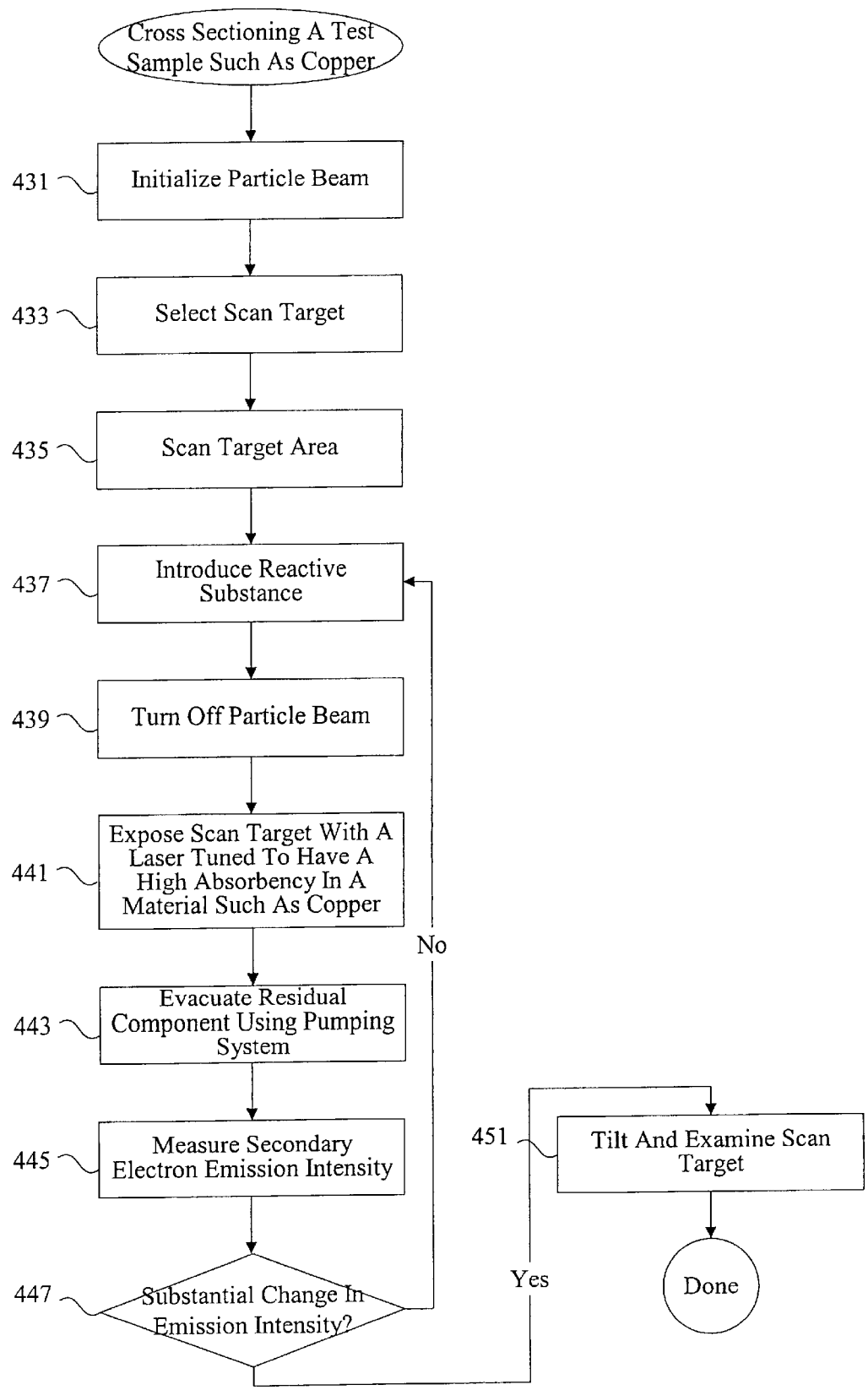
Figure 5:
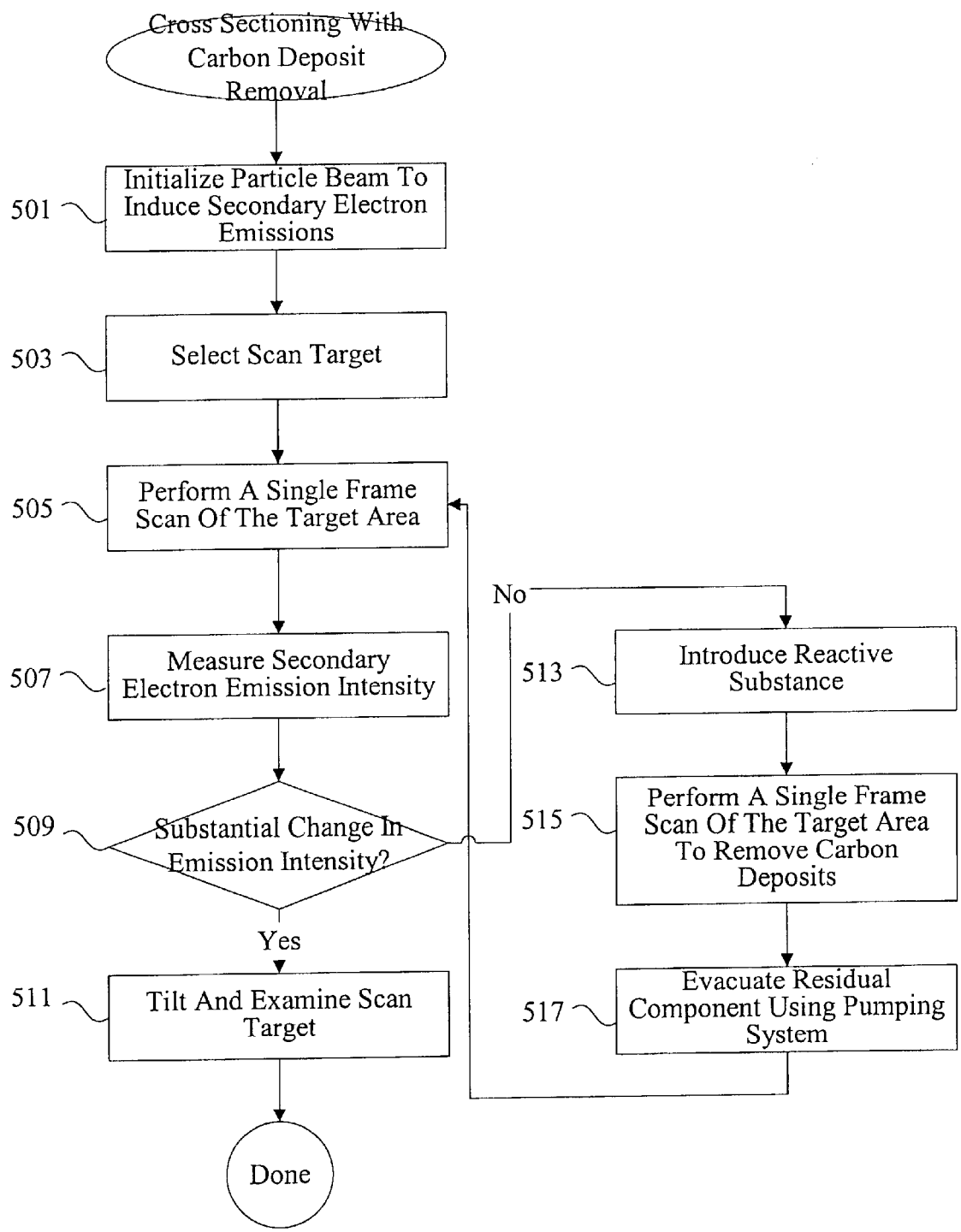
FIGS. 5 is a process flow diagram showing the scanning of a sample to remove impurities.

FIG. 4B is a flow process diagram showing techniques for cross-section in a test sample by removing a copper layer. At 431, the electron beam is initialized. In one example, the electron beam is initialized with high currents and low landing energy parameters to induce a substantial number of secondary electron emissions from a scan target. Typical techniques such as ion beam induced etching and gas assisted ion beam induced etching do not attempt to cause the emission of a substantial number of secondary electrons from a scan target. Other techniques use high energy electron beams with various gases to etch away material without measuring or tuning for secondary electron emissions.

According to various embodiments, techniques of the present invention use electron beams specifically tuned to induce secondary electron emissions. Typical electron beam scanning techniques do not provide for tuning the beam specifically to induce secondary electron emissions. At 433, the scan target is selected and at 435 target area is scanned using the electron beam. At 437, a reactive substance is introduced. To remove copper, a reactive substance such as a gas including a chlorine component is introduced at the target area. When a chlorine component in a gas interacts with an electron beam and a copper layer, copper chloride is generated. However, copper chloride can not easily be evacuated using a pumping system because copper chloride has a poor vapor pressure.

To remove the residual component copper chloride, the target area is exposed with a laser tuned to have a high absorbency in copper chloride, and very low absorbency in copper (300–350 nm). In one example, an electron beam is turned off first at 439. At 441, the scan target is exposed using a specifically tuned laser. At 443, any residual components are evacuated using a system such as a pumping system. At 445, secondary electron emission intensity is measured. At 447, it is determined whether there is a substantial change in secondary electron emission intensity between a current measurement and a prior measurement, or the current through the substrate,. Any change indicating that a different material is interacting with the electron beam is referred to herein as a substantial change in secondary electron emission intensity. If there is a substantial change, the reactive substance is again introduced at 437.

The residual components are removed by exposing the scan target with a laser and subsequently evacuating the residual components using a system such as a pumping system. The process of introducing a reactive substance and removing residual components is repeated until there is a substantial change in secondary electron emission intensity. When it is determined that there is a substantial change, the scan target is examined at 451. In one example, the scan target is tilted to allow a sunset look at the scan target.

Although the techniques of the present invention can be used to remove the layer such as a copper layer, the techniques can also be used to remove contaminants in the scan target. According to various embodiments, electron beams cause carbon layers to form in scan targets. These hydrocarbon or carbon layers affect the intensity of secondary electron emission measurements from a scan target. Furthermore, carbon layers can also interfere with the adhesion of a copper layer onto a copper seed layer. Techniques are provided for removing carbon deposits continually generated during electron beam scans. At 501, an electron beam is initialized to induce secondary electron emissions from a scan target. At 503, the scan target is selected. At 505, the target is scanned at a rate of 60 hertz.

In one example, a single frame scan is performed on the target area. In other examples, a target is scanned for a specified period of time. At 507, secondary electron emissions are measured. If there is a substantial change in emission intensity at 509, the scan target is examined at 511. If there is a change in emission intensity, a reactive substance is introduced to remove carbon deposits at 513. In one example, oxygen is introduced. The oxygen reacts with carbon deposits to form the residual component $CO_2$. At 515, the scan target is scanned using the electron beam to allow the electrons to interact with carbon deposits and the oxygen introduced. In one example, a single frame scan is performed.

In other examples, the scan target is scanned for a predetermined time period. At 517, residual components are removed. It should be noted, that introducing the reactive substance to carbon deposits can be used in conjunction with techniques for etching away various layers in the scan target. In one example, a copper layer is etched away as described in FIG. 4B. while carbon deposits are continually removed from the scan target.

The techniques of the present invention allow nondestructive cross sectioning of a test sample. It should be noted that the techniques can be used in conjunction with other techniques to inspect a sample.

Figure 6:
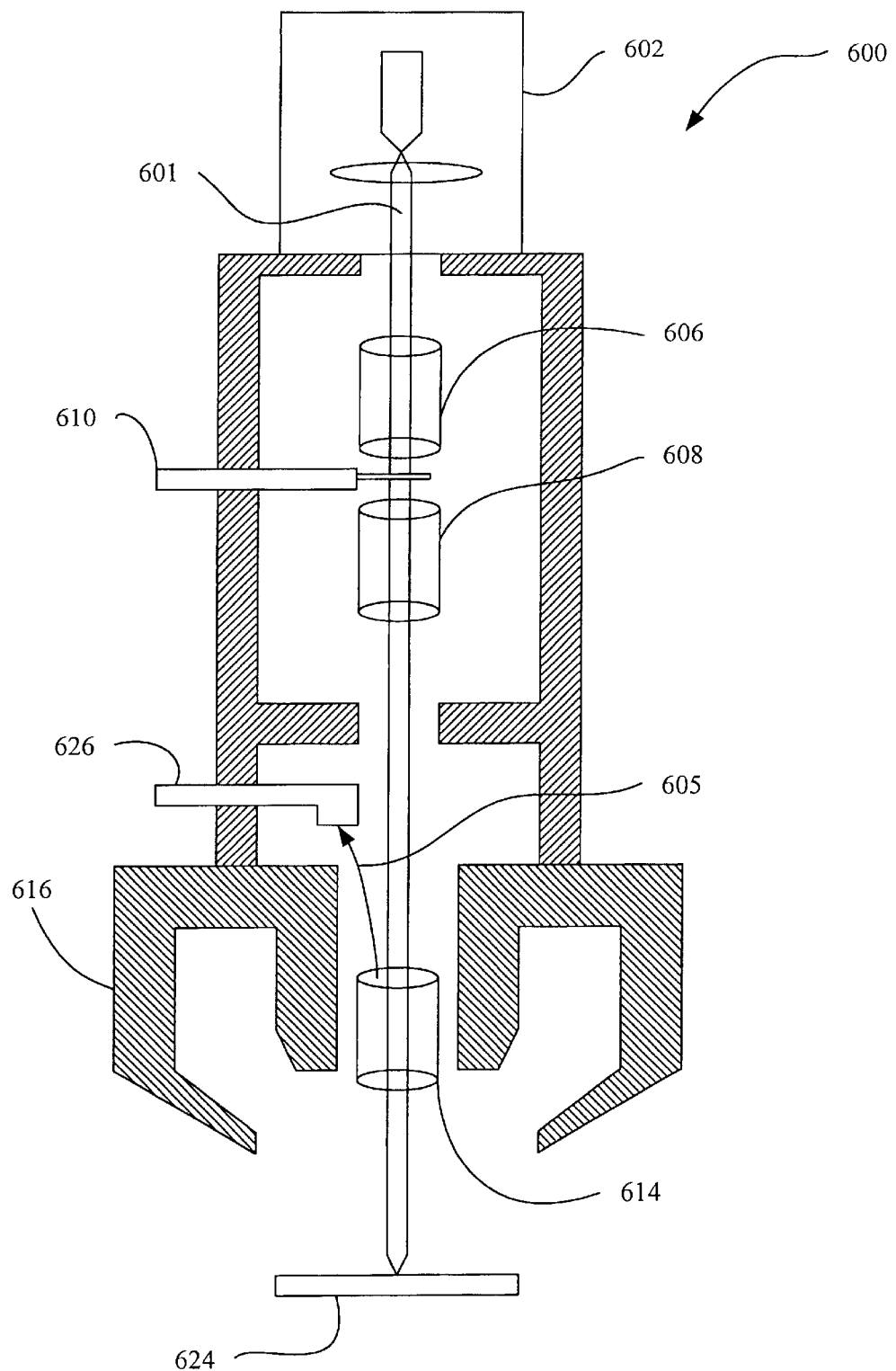
FIG. 6 is a diagrammatic representation of an electron beam generator that can be used to implement scanning of a sample.

An electron beam may be anything that causes secondary electrons to emanate from the sample under test. In one embodiment, the electron beam can be a scanning electron microscope (SEM). FIG. 6 is a diagrammatic representation of a scanning electron microscope (SEM) 600. As shown, the SEM system 600 includes an electron beam generator (602 through 616) that generates and directs an electron beam 601 substantially toward an area of interest on a specimen 624.

In one embodiment, the electron beam generator can include an electron source unit 602, an alignment octupole 606, an electrostatic predeflector 608, a variable aperture 610, a wien filter 614, and a magnetic objective lens 616. The source unit 602 may be implemented in any suitable form for generating and emitting electrons. For example, the source unit 602 may be in the form of a filament that is heated such that electrons within the filament are excited and emitted from the filament. The octupole 606 is configured to align the beam after a particular gun lens voltage is selected. In other words, the beam may have to be moved such that it is realigned with respect to the aperture 610.

The aperture 610 forms a hole through which the beam is directed. The lower quadrupole 608 may be included to compensate for mechanical alignment discrepancies. That is, the lower quadrupole 608 is used to adjust the alignment of the beam with respect to any misaligned through-holes of the SEM through which the beam must travel. The magnetic objective lens 616 provides a mechanism for fine focusing of the beam on the sample.

Figure 7:
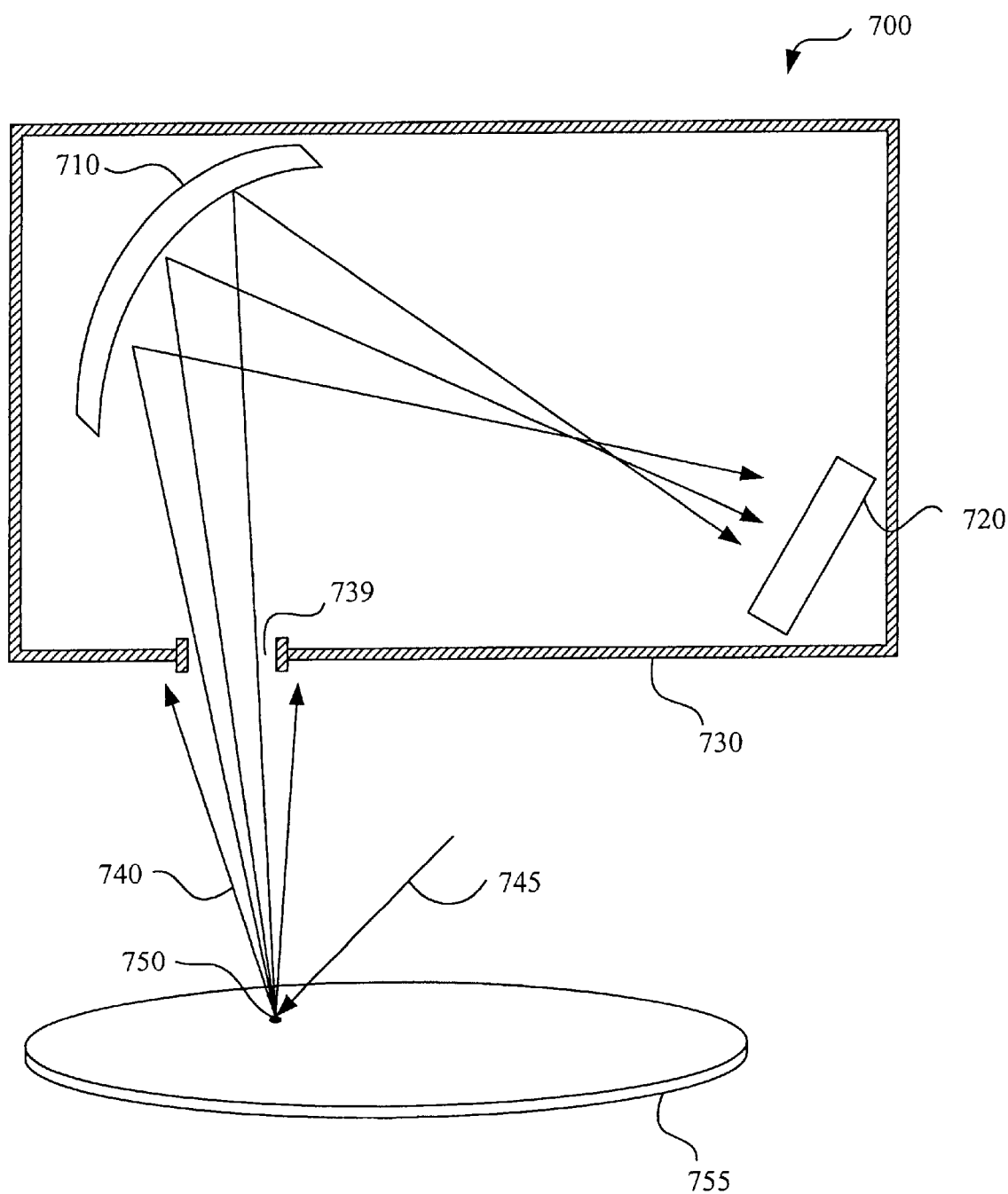
FIG. 7 is a diagrammatic representation of a detector that can be used to measure secondary electron emissions.

Any suitable detector for measuring secondary electrons may be used to detect secondary electrons emitted from the sample. In one example, three detectors are tuned to individually measure the intensities of Cu, T, and N emissions. FIG. 7 is a cross-sectional representation of a wavelength dispersive system (WDS) secondary electron detector in accordance with one embodiment of the present invention.

Each secondary electron detector 700 includes a housing 730 having an aperture 739. The housing and aperture are optional for practicing the techniques of the present invention. An electron beam 745 is directed to a focus point 750 on a thin film device 755 (i.e., a semiconductor wafer). The electron beam 745 causes electrons 740 to emanate from the focus point 750. The aperture 739 permits a limited amount of electrons 740 to enter each detector 700. Upon entering the detector 700, each electron travels along a path to a concave reflective surface 710. The reflective surface 710 directs a portion of electrons to a sensor 720.

Figure 8:
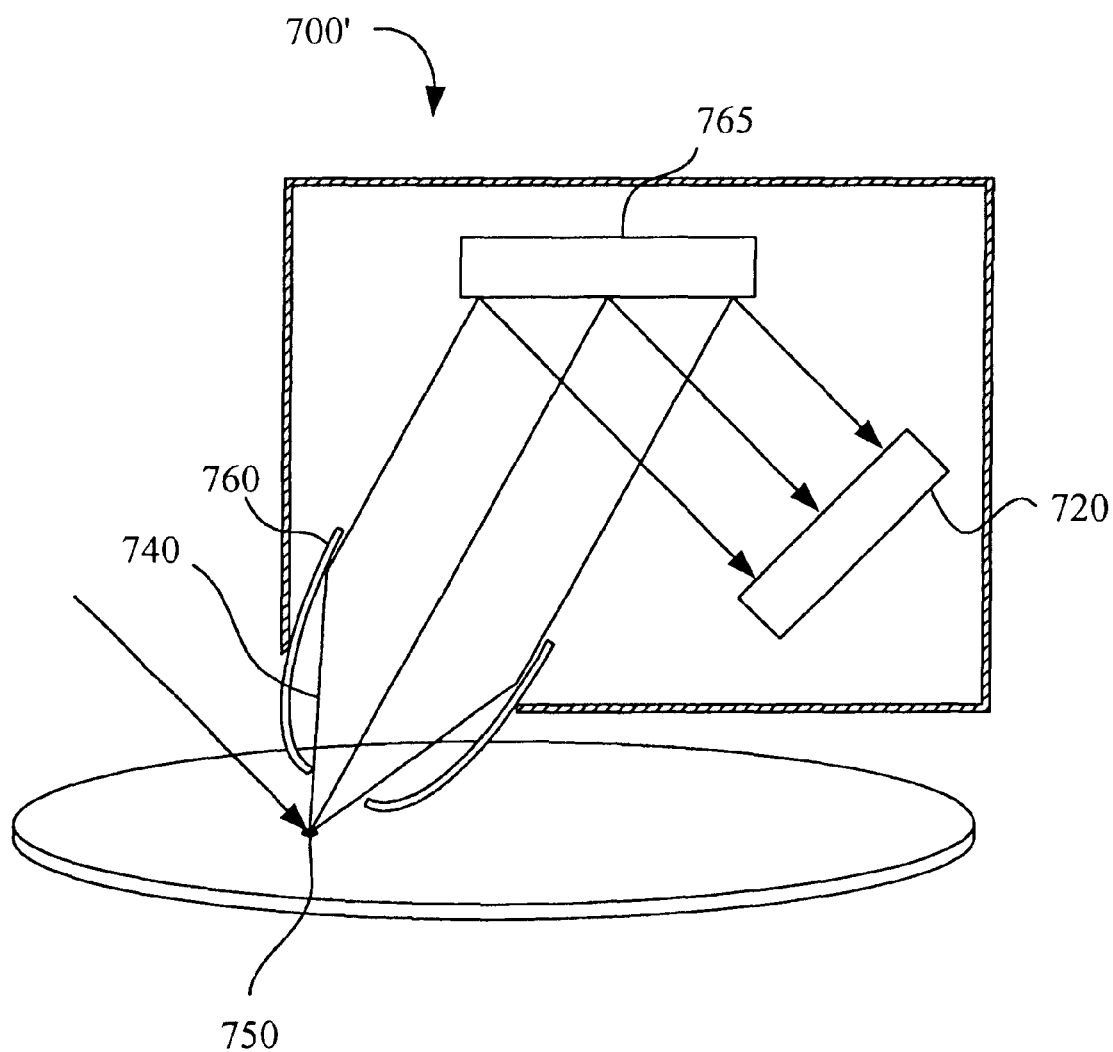
FIG. 8 is a cross-sectional view of a detector that can be used.

A cross-sectional view of an alternative embodiment of a WDS secondary electron detector 700' is illustrated in FIG. 8. Detector 700' has a collimator 760 that captures the electrons 740 emanating from the focus point 750, and then through its reflective surfaces causes the electrons 740 to travel in substantially parallel paths. The collimator 760 is generally made from metal foil material. The electrons then reflect off of a substantially flat reflective surface 765 such that the electrons 740 continue in parallel paths towards the sensor 720. Similarly with detector 700, the reflective surface 765 in detector 700' may also be Bragg reflector or a crystal.

The test system of the illustrated embodiment is capable of obtaining measurements having 0.5% precision with measurement times of 2 to 20 seconds. Thus, the test system allows for both accurate characterization and a high throughput rate.

Although the foregoing invention has been described in some detail for purposes of clarity of understanding, it will be apparent that certain changes and modifications may be practiced within the scope of the appended claims. The techniques of the present invention can be applied to measuring multiple layers of thin-films and determining the composition of thin films.

It should be noted that there are many alternative ways of implementing the techniques of the present invention. For example, prior to performing comparisons between secondary electron emission measurements and control measurements, an entire wafer may be scanned and the corresponding emission measurements stored. The comparisons can then be performed after the entire wafer is scanned and the control measurement can be determined using emission measurements from the entire wafer. Accordingly, the present embodiments are to be considered as illustrative and not restrictive, and the invention is not to be limited to the details given herein, but may be modified within the scope and equivalents of the appended claims.

What is claimed is:

1. A method for inspecting a test sample, the method comprising:
    scanning a first scan target in a test sample by using an electron beam generator configured to emit particles with a first landing energy, wherein the first landing energy causes secondary electron emissions from the first scan target;
    introducing a reactive substance and removing a residual component at the first scan target during a first period of time; and
    measuring the intensity of secondary electron emissions during a second period of time.

2. The method of claim 1, wherein introducing the reactive substance during the first period of time removes carbon contamination.

3. The method of claim 1, wherein measuring the intensity of secondary electron emission during the second period of time allows measurements substantially free of carbon contamination.

4. The method of claim 1, wherein the first period is a single scan frame.

5. The method of claim 1, wherein the second period is a single scan frame.

6. The method of claim 1, wherein removing the residual component comprises removing the carbon continuously introduced by the scanning of the first scan target.

7. The method of claim 1, wherein the residual component is removed by evacuating the residual component using a pumping system.

8. The method of claim 1, wherein the residual component is removed by exposing the first scan target with a laser.

9. The method of claim 7, wherein the laser is tuned to a wavelength having high absorbency in the residual component.

10. The method of claim 9, wherein the laser is tuned to a wavelength having high absorbency in copper chloride and a low absorbency in copper.

11. The method of claim 1, wherein a substantial change in measured secondary electron emission intensity comprises a substantial change in color and contrast of secondary electron emissions.

12. The method of claim 1, wherein a substantial change in intensity indicates that a layer in the first scan target has been removed.

13. The method of claim 9, further comprising scanning the first scan target without introducing the reactive substance after a substantial change in secondary electron emission intensity is measured.

14. The method of claim 13, further comprising tilting the sample and scanning at an acute incident angle while scanning the first scan target.

15. The method of claim 1, wherein the reactive substance is a reactive gas.

16. The method of claim 1, wherein the reactive substance interacts with the electrons to etch away material at the first scan target.

17. The method of claim 1, wherein the first landing energy is selected to maximize secondary electron emissions from the first scan target.

18. The method of claim 1, wherein the first scan target is a portion of a wafer populated with integrated circuits.

19. A apparatus for characterizing a sample, the apparatus comprising:

an electron beam generator operable to scan a first scan target in a sample using electrons with a first landing energy, wherein the electron beam generator induces secondary electron emissions from the first scan target;

a reactive substance injector operable to introduce a reactive substance near the first scan target in order to remove carbon from the first scan target during periodic intervals;

a secondary electron emission detector configured to measure the intensity of secondary electron emissions between the periodic intervals.

20. The apparatus of claim 19, wherein the periodic interval is a single frame of a scan.

21. An apparatus for inspecting a test sample, the apparatus comprising:

means for scanning a first scan target in a test sample with electrons with a first landing energy, wherein the first landing energy causes secondary electron emissions from the first scan target;

means for introducing a reactive substance and removing a residual component at the first scan target during a first period of time; and means for measuring the intensity of secondary electron emissions during a second period of time.

22. The apparatus of claim 21, wherein introducing the reactive substance during the first period of time removes carbon contamination.

23. The apparatus of claim 22, wherein measuring the intensity of secondary electron emission during the second period of time allows measurements substantially free of carbon contamination.

* * * * *